United States Patent
Kaplan et al.

[11] Patent Number: 6,162,238
[45] Date of Patent: Dec. 19, 2000

[54] APPARATUS AND METHODS FOR CONTROL OF BODY LUMENS

[75] Inventors: Aaron V. Kaplan, 851 Carnation Ct., Los Altos, Calif. 94024; Nubar S. Manoukian, Cupertino, Calif.; Darel E. Hodgson, Palo Alto, Calif.; Jordan T. Bajor, Palo Alto, Calif.

[73] Assignee: Aaron V. Kaplan, Los Altos, Calif.

[21] Appl. No.: 09/256,816

[22] Filed: Feb. 24, 1999

[51] Int. Cl.[7] ............................................. A61B 17/00
[52] U.S. Cl. ................................................ 606/201; 604/9
[58] Field of Search .............................. 606/201; 623/26; 600/31, 30; 417/412; 128/885; 604/8, 9

[56] References Cited

U.S. PATENT DOCUMENTS

| | | | |
|---|---|---|---|
| 3,538,917 | 11/1970 | Selker | 604/9 |
| 3,939,821 | 2/1976 | Roth | 604/9 |
| 4,053,952 | 10/1977 | Goldstein | 3/1.1 |
| 4,556,050 | 12/1985 | Hodgson et al. | 128/1 |
| 5,324,315 | 6/1994 | Grevious | 607/60 |
| 5,354,319 | 10/1994 | Wyborny et al. | 607/32 |
| 5,466,242 | 11/1995 | Mori | 606/198 |
| 5,480,431 | 1/1996 | Freitag et al. | 623/9 |
| 5,556,414 | 9/1996 | Turi | 606/198 |
| 5,562,713 | 10/1996 | Silvian | 607/32 |
| 5,562,714 | 10/1996 | Grevious | 607/32 |
| 5,861,019 | 1/1999 | Sun et al. | 607/60 |

Primary Examiner—Michael Buiz
Assistant Examiner—Jackie Tan-Uyen T Ho
Attorney, Agent, or Firm—Townsend and Townsend and Crew LLP

[57] ABSTRACT

Implantable systems for controlling flow through body lumens comprise a control module and an actuator. The actuator is implanted at least partially over the body lumen to selectively constrict the lumen and control flow therethrough. The control module includes at least a power source for operating the actuator and a remotely operated switch for controlling the power source. Usually, the control module will have programmable circuitry for adjusting on/off time, degree of closure, and the like. The switch of the control module is remotely actuated by a magnetic or other signal. The control circuitry may be remotely programmed using a hand-held programmer.

19 Claims, 6 Drawing Sheets

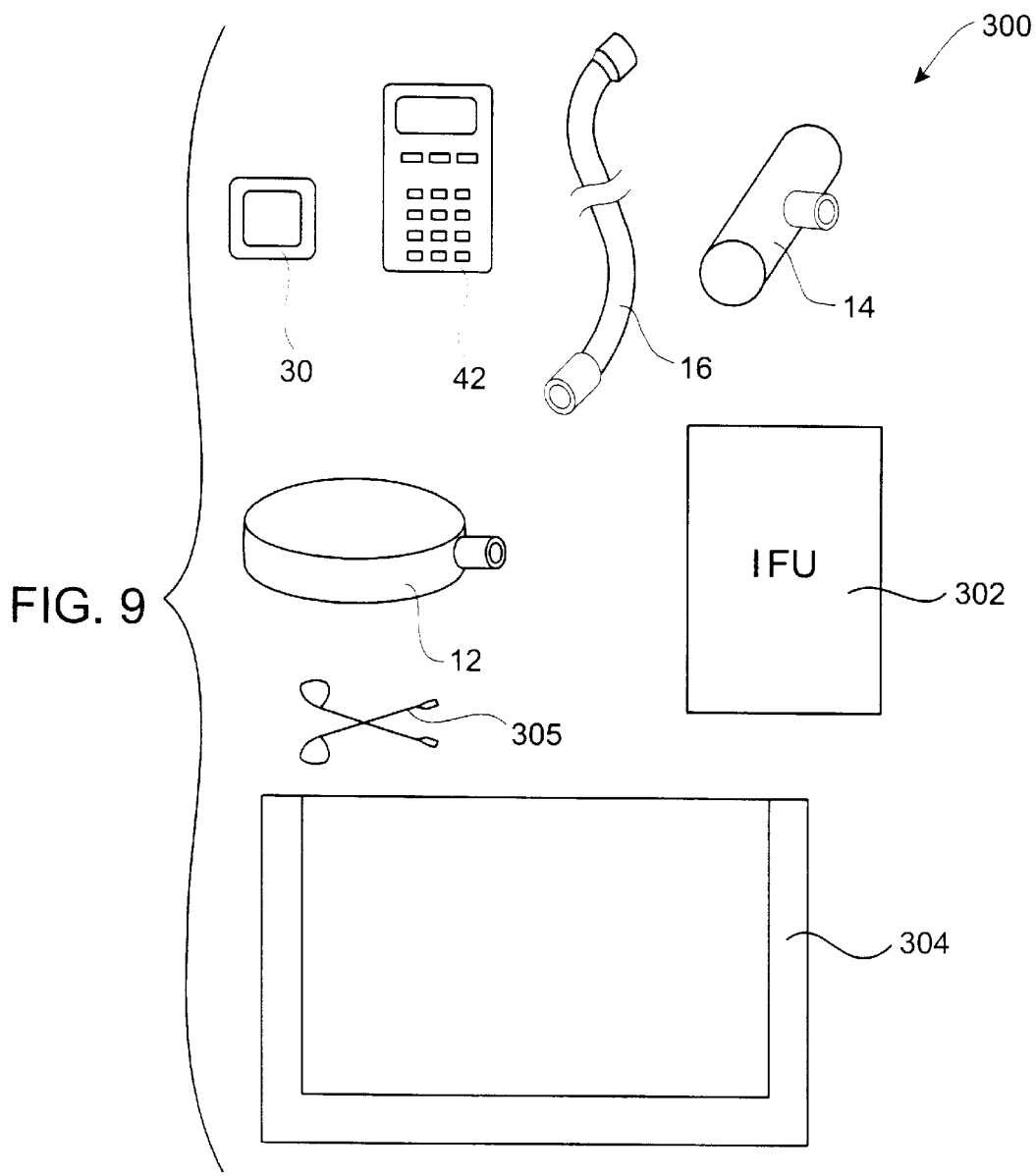

APPARATUS AND METHODS FOR CONTROL OF BODY LUMENS

BACKGROUND OF THE INVENTION

1. The Field of the Invention

The present invention relates generally to medical apparatus and methods. More particularly, the present invention relates to apparatus and methods to permit external control of flow through internal body lumens.

Urinary incontinence is a significant problem for a number of adult men and women throughout the world. Severe cases of urinary incontinence may be treated by implantation of an artificial sphincter which comprises an inflatable cuff placed around the urethra, particularly in men. The cuff may be selectively inflated and deflated through use of a remote pump module which is subcutaneously implanted and manipulated through the skin. Although effective to some extent, such manually inflatable systems have a number of drawbacks. Implantation of the pump is difficult and locations where the pump may be actuated through the skin are limited, particularly in women. Many patients find it difficult to manually actuate the pump through the skin, and subsequent modification and adjustment of the pump system generally requires a repeat operation.

For all these reasons, it would be desirable to provide alternative and/or improved implantable systems for selectively controlling flow through the urethra and other body lumens. Such systems should be relatively easy to implant, should permit straight forward and reliable operation by the patient, should have a long life, and should permit convenient reprogramming and/or system interrogation without the need to surgically access the implanted component(s) of the system. At least some of these objectives will be met by the invention described hereinafter.

2. Description of the Background Art

U.S. Pat. No. 4,556,050, describes an artificial sphincter which is implantable about a body lumen. The sphincter includes a shape memory component which can be opened by applying power through an implanted pick-up coil. U.S. Pat. Nos. 5,556,414; 5,480,431; and 5,466,242, describe stents having shape memory components which can be reconfigured by applying energy.

SUMMARY OF THE INVENTION

The present invention provides systems, methods, and kits for treating patients suffering from urinary incontinence and other conditions which are caused by the inability to open or close a body lumen. Control of urinary incontinence is effected by opening and closing the patient's urethra, as will be described in detail below. Other body lumens which can be opened and closed according to the present invention include the rectal sphincter, the lower esophageal sphincter, the ampulla of vater, fallopian tube, vas deferens, and the like. The advantages of the present invention include simplicity of operation, i.e., there is generally no need for manipulation of any part of the system through the skin. The systems are highly reliable and easy to implant, usually being suitable for implantation in the doctor's office. The systems are amenable to easy adjustment and reprogramming, even after implantation, and can be easily interrogated to determine system status. Additionally, the systems will be equally suitable for both male and female anatomy.

Systems according to the present invention comprise a control module and a separate actuator. The control module includes a power source and a remotely operated switch which controls a power output from the power source. The actuator is connectable to the control module to receive power from the power output, typically by a separate electrical or other lead. The actuator is implantable on, over, or adjacent to the exterior of the target body lumen and may be shifted between an open configuration where the body lumen is at least partially open and a closed configuration where the body lumen is at least partially closed. The actuator shifts between these two configurations in response to a change in power from the power output controlled by the switch in the control module. Thus, by remotely controlling the switch to turn on or off the power, or otherwise modulate the power, the actuator can selectively effect opening and closing of the body lumen.

The remotely operated switch can take a variety of configurations. Desirably, the switch will be capable of "wireless" operation, i.e., the switch command will be transmitted through the skin to the implanted control module to change the switch status. In a simple and presently preferred configuration, the switch actuator can be a permanent magnet which, when placed over the skin adjacent to the control module, will operate a magnetically responsive switch. Optionally, the magnet may be an electromagnet so that the user must not only place the magnet in proximity to the implanted control module, but must also depress a button or other device to effect operation. A variety of other remotely operated switches and remote switch actuators will also be possible, including ultrasonic switches, radiofrequency switches, microwave switches, and the like.

The system will typically further comprise an implantable lead which connects the power output of the control module to the actuator. The lead may be permanently affixed to either or both of the control module and actuator, but will more usually be separate from, but connectable to both the control module and the actuator. The lead will usually be an electrical lead permitting the transmission of electrical power between the control module and the actuator. In other circumstances, however, the lead may be suitable for hydraulic or pressure communication between the control module and the actuator. It would further be possible to provide mechanical linkages, e.g., reciprocating rods, rotating cables, or the like. But such mechanical power transmission will generally not be preferred.

In a preferred embodiment, the control module will further include a programmable component which permits the user to vary or modulate at least one variable, such as opening time, opening diameter, opening force, closing force, and the like. Preferably, the programmable component of the control module may be remotely programmed after the module is implanted. The system will then further comprise a remote programmer which can communicate with and download program information to the programmable component, typically via an ultrasonic, radiofrequency, microwave, or other suitable transmission signal. Such communication will preferably be wireless, but in some instances it might be possible to utilize percutaneous leads which are temporarily introduced through the skin to contact the implanted control module.

Optionally, the programmer may also be adapted to interrogate the implanted control module to determine system status, e.g., the opening time set point, the opening diameter set point, remaining battery life, use history, and the like. In such cases, the control module will include a transmission component for signaling system status to the programmer.

The design of the actuator may vary widely. Generally, it is necessary only that the actuator be able to receive power from the implanted control module and convert or otherwise utilize the power to open and close the body lumen, typically by modulating a compressive or constraining force over the exterior of the body lumen. In a first exemplary embodiment, the actuator comprises a base, a sling attached to the base which defines a loop for receiving the body lumen, i.e., mounting over the body lumen. The system further includes a motor attached to the sling in such a way that it can open and close the loop. The motor will usually be operated based on an electrical output from the power source in the control module. Alternatively, hydraulic motors could be supplied as described in connection with a later embodiment.

A second embodiment of the actuator comprises a mechanical cuff which may be mounted over the exterior of the body lumen. The cuff is typically spring biased to remain closed. A shape memory opening element on the cuff can receive an electrical output from the power source to open the cuff against the spring bias. It would, of course, be possible to configure the cuff so that the spring bias opens it over the body lumen, but such a design would require that the closing power be applied substantially continuously during all periods when it is desired that the body lumen be closed. Such a design would not be desirable for systems intended to treat urinary incontinence.

In a third embodiment, the actuator comprises an inflatable cuff which can receive a pressurized inflation medium from the control module. Typically, an electrically actuated bellows movement can provide opening and closing pressure to the cuff.

Methods according to the present invention for opening and/or closing a body lumen comprise signaling a command to an implanted control module. The control module controls energy from a power source within the control module to open or close an actuator which is implanted to selectively constrain (or release from constraint) the body lumen. Preferably, signaling causes the control module to energize the actuator which in turn causes the actuator to open (release constraint from) the body lumen. In some instances, the control module will deliver energy for a predetermined time period in response to the initial signal, and the actuator will close after the predetermined time signal without any further signal. Alternatively, the actuator programming could be configured so that, once open, it remains open until receiving a close signal. The methods may utilize actuators which are biased either opened or closed in an unenergized configuration. In such instances, energy will be delivered to either close or open the actuator, respectively. Alternatively, the actuator may be provided with latches so that it will remain opened or closed after being switched to either position. Such systems will generally not be biased (although they can be partially biased to reduce the energy required for shifting) and must be switched between the opened and closed configurations, but will generally not require continuous energy to maintain either configuration.

The present invention still further comprises methods for implanting systems which selectively open and close a body lumen. The methods comprise implanting an actuator over, adjacent to, or otherwise so that it can constrain the body lumen. The actuators have at least an opened and a closed configuration, and may optionally have variable positions between fully opened and fully closed. The methods further comprise implanting a control module having a power source and a remotely operated switch. The switch controls power from a power output to the implanted actuator. A lead is further implanted between the actuator and the output of the power source in order to complete the system. The systems may then be operated by the techniques described above in connection with the system.

The present invention still further comprises kits. A first exemplary kit includes an actuator, a control module, and a remote switch actuator, together with instructions for use according to the methods of the present invention. A second exemplary kit comprises an actuator, a control module, and a lead connectable between the actuator and the control module, and further comprises instructions for implantation according to any of the methods described above. Either or both kits may further comprise implantation tools, programmers, or the like.

BRIEF DESCRIPTION OF THE DRAWINGS

FIG. 9 illustrates a kit comprising the components of the system of FIG. 1.

DESCRIPTION OF THE SPECIFIC EMBODIMENTS

Figure 1:
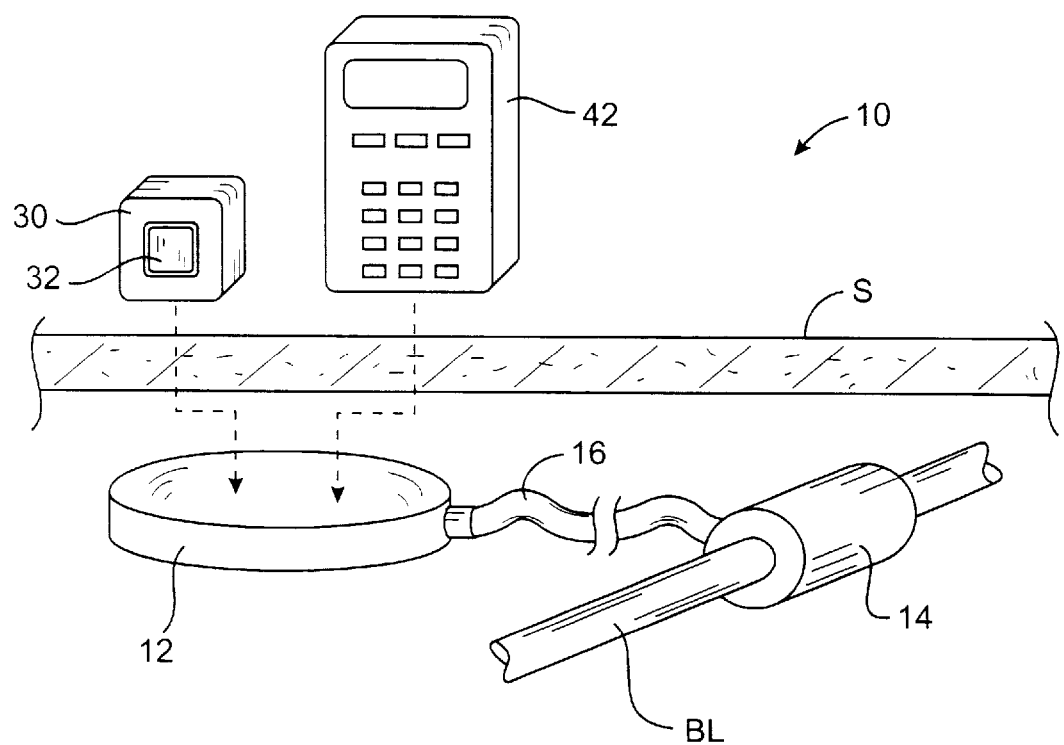
FIG. 1 is a schematic illustration of a system constructed in accordance with the principles of the present invention, including a control module, an actuator, a lead for connecting the control module to the actuator, a remote switch, and a remote programmer.

Referring to FIG. 1, systems can according to the present invention comprise at least a control module 12 and an actuator 14 which are implantable beneath the skin S of a patient by conventional surgical techniques. Usually, the control module 12 and actuator 14 will be separate components and will be implanted at separate locations, but in some instances both such components will be combined integrally in a single housing for implantation at a single site. When separate, the actuator 14 will be implanted at least partially over a target body lumen BL, typically the urethra, the rectal sphincter, the lower esophageal sphincter, the ampulla of vater, fallopian tube, vas deferens, or the like. The control module 12 will be implanted at a location remote from the body lumen, typically within a subcutaneous space (relatively close to the skin surface), typically within 0.5 cm to 10 cm of the skin surface. The actuator 14 and control module 12 will usually be implanted in separate surgically created tissue spaces and will be connected by a lead 16 which may be placed by tunneling between the two separate implantation sites. Usually, the lead will have connectors at each end so that it may be removably connected to both the actuator 14 and control module 12. Thus, if for any reason any one component of the system needs to be replaced, it will not be necessary to remove each of the components. The nature of the lead will depend on the manner in which the control module 12 powers and controls the actuator 14, as described in more detail below.

Figure 2:
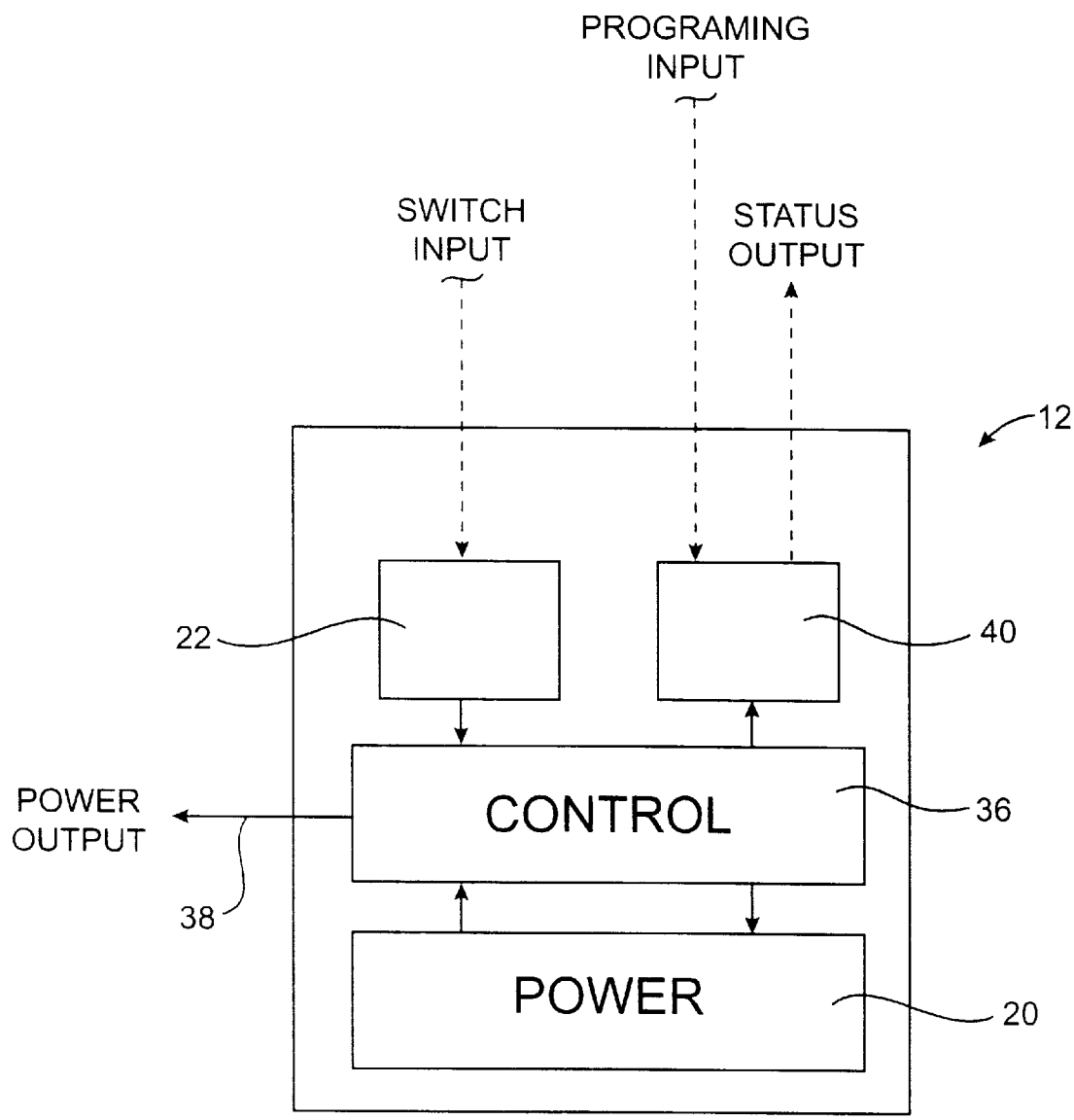
FIG. 2 is a schematic illustration of the control module of FIG. 1.

Referring now to both FIGS. 1 and 2, the control module 12 will include a power source 20 and a remotely signaled or actuated switch 22. The power source will usually be a battery, such as a battery of the type commonly used in cardiac pacemakers. The power source could also be a mechanical movement, such as the mechanical movements used in subcutaneous drug infusion pumps. These movements are similar to those employed in self-winding watches and rely on the mechanical conversion of kinetic energy into stored energy in a spring or other storage mechanism. In the exemplary case of a battery, the remotely signaled switch may be directly connected to the battery and comprise a simple on/off mechanism. For example, the switch could be a two-position switch which can be changed from on to off by exposure to a signal, such as a magnetic signal provided by a permanent or electromagnet. Alternatively, the remotely signaled switch could correspond to a wireless electronic, ultrasonic, or other signal. A remote switch actuator 30 having a actuation button 32 is illustrated in FIG. 1.

In addition to power and an on/off switch, the control module 12 may include control circuitry 36 for controlling a power output signal 38 in a variety of ways. The control circuitry 36 may be a simple digital or analog circuit for controlling such variables as timing, i.e., a fixed or variable time output for the power signal based on a single input from the input switch 22. Other variables include the diameter or closure force provided by the actuator 14, and the like. The control circuitry 36 may be "hard wired" so that it is not adjustable in the field and/or after implantation. Preferably, however, it will be programmable at least prior to implantation and more preferably both prior to implantation and after implantation. To permit reprogramming after implantation, the control module 12 will include a signal receiver 40 which communicates with an external programming unit 42 (FIG. 1). Usually, the signal receiver 40 will also provide for transmission back to the programming unit 42 so that certain status variables of the control module 12 may be interrogated, e.g., opening time, battery life, opening diameter, opening force, closing force, use history, and the like. Communication between the remote programmer 42 and the receiver/transmitter 40 may be by any conventional mode, such as ultrasonic, radiofrequency, microwave, optical, or the like. For example, data may be transferred using a radiofrequency telemetry system as described in U.S. Pat. No. 5,861,019, the full disclosure of which is incorporated herein by reference.

The actuator 14 may have a wide variety of designs. Usually, the actuator 14 will be powered by the output of the control module 12, either electrically, hydraulically, mechanically, or the like. The actuator may be active, i.e., require power to be maintained in either an open or a closed (or partially opened or partially closed) configuration, or may be passive, i.e., being capable of latching in either position and requiring power only to switch between two or more latched configurations. The actuator 14 will be able to constrict the body lumen, usually by providing a circumferential structure which closes over the body lumen. Alternatively, the actuator 14 could be a hinged structure which squeezes the body lumen, could be a parallelogram structure which closes over the body lumen, or have a wide variety of other configurations.

Figure 3:
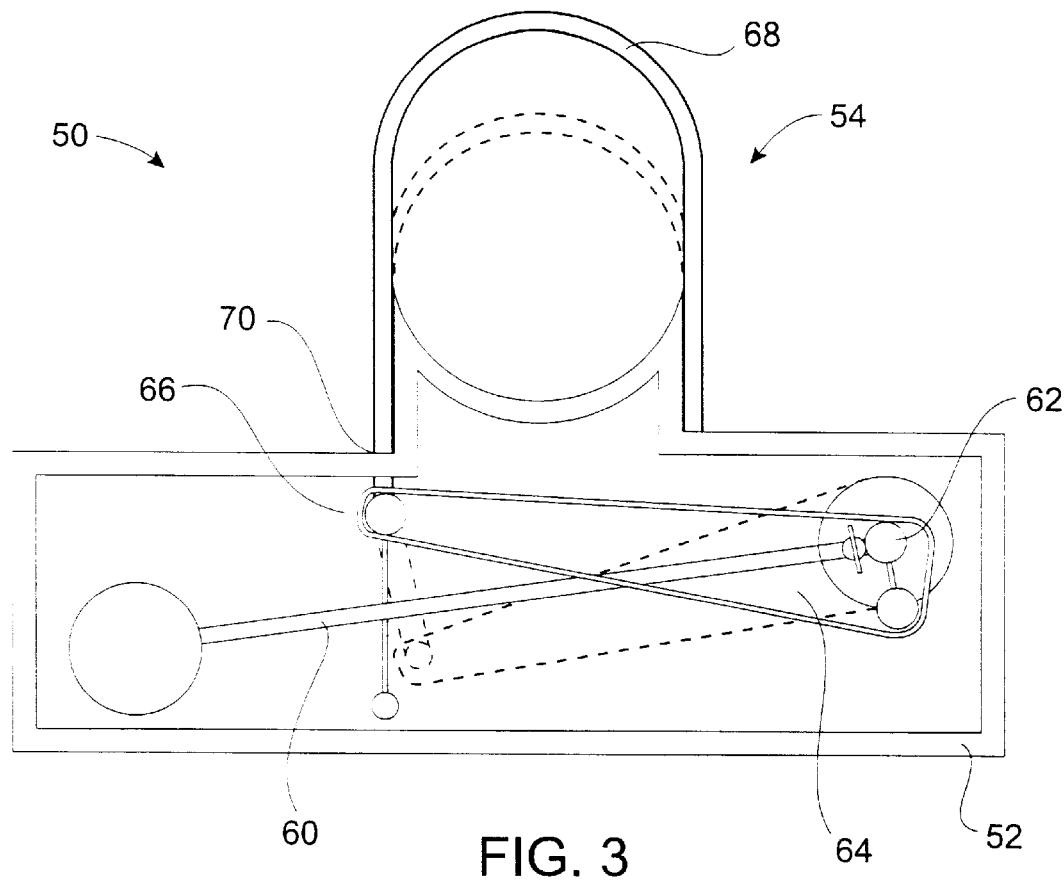
FIG. 3 illustrates a first embodiment of an actuator suitable for use in the system of FIG. 1.

Referring now to FIG. 3, an actuator 50 comprises a motor section 52 and a sling section 54. The motor is designed to receive electrical power from the control module 12 via the lead 16 (not shown in FIG. 3). The motor is driven by a shape memory alloy wire 60 which is fixed at one end and connected to a lever 62 at the other end. By applying electrical power to the wire 60 from the control module 12, the wire will shorten, pulling lever 64 downwardly, as shown in broken line. A distal end 66 of the lever is attached to a band 68 which defines the sling 54. By pulling down on a free end of the band 68, the sling is tightened, also as shown in broken line. The band passes through a hermetic seal 70 in the housing of the motor 52. Although this embodiment is shown to require power for closing, it could easily be reconfigured to require power for opening by reversing the action of the lever.

Figure 4:
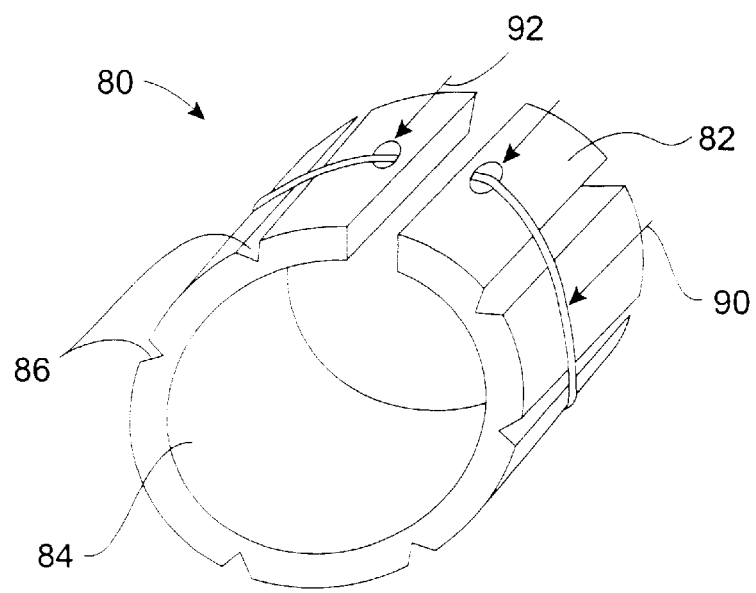
FIG. 4 illustrates a second embodiment of an actuator suitable for use in the system of FIG. 1.

A second embodiment 80 for an actuator is shown in FIG. 4. The actuator 80 comprises a cuff 82 having a passage 84 therethrough which may be placed over the target body lumen. Cuff 82 is formed from a spring material so that it has a first diameter when in its relaxed configuration. As illustrated, the spring may be formed from stainless steel, nickel titanium alloy, or a polymeric material, and will usually have a series of axial channels 86 which facilitate its closure (or opening). The cuff 82 is opened by a shape memory wire 90, typically a nickel titanium wire which is connected to the power output of the control module 12 (not illustrated). The wire 90 will be configured so that the application of energy causes the wire to shorten, thus increasing the diameter of cuff 82. In this way, the cuff 82 can open the body lumen. The actuator 80 will thus open when powered, but could also be configured to close when powered by reconfiguring the wire 90 so that it closes (decreases the diameter) when power is applied.

Figure 5:
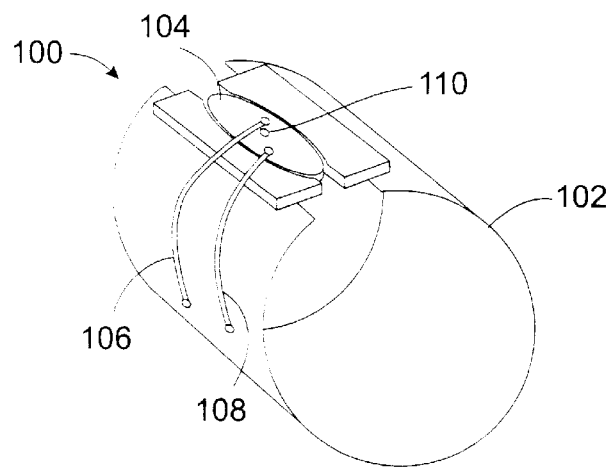
FIG. 5 illustrates a third embodiment of an actuator suitable for use in the system of FIG. 1.

A third actuator 100 is illustrated in FIG. 5. A spring cuff 102 is held together by a cam mechanism 104. The cam 104 is controlled by shape memory wires 106 and 108 attached to sides of the cam opposite a pivot point 110. Wire 106 is configured so that application of energy (from the control module 12) will shorten the wire, causing the cam to pivot and push the cuff 102 open. The cam 104 will then remain in its open configuration until power is applied to the second wire 108 to pull the cam back to the closed position.

Figure 6:
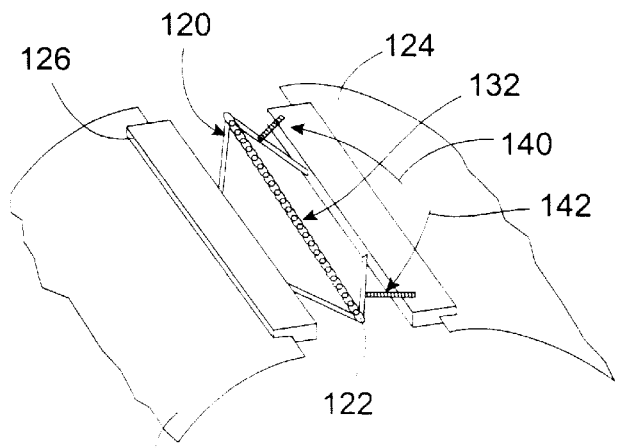
FIGS. 6 and 7 illustrate a fourth embodiment of an actuator suitable for use in the system of FIG. 1.
Figure 7:
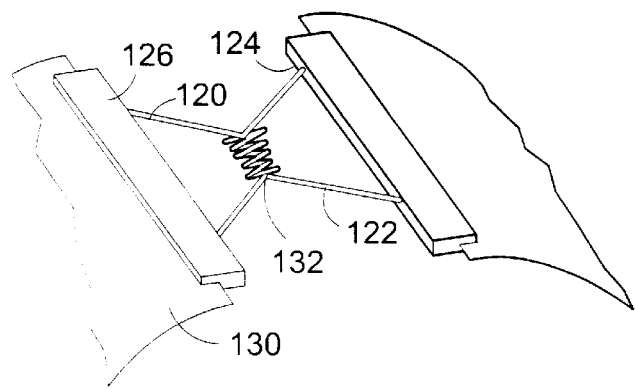

A similar cuff opening mechanism is illustrated in FIGS. 6 and 7. The mechanism comprises opposed scissor mechanisms 120 and 122 attached to fixtures 124 and 126 on the edges of a cuff 130. A shape memory spring 132 is secured between the apices of the scissor mechanisms 120 and 122 so that it may be opened by applying energy to the spring, thus shortening the spring as shown in FIG. 7. Optionally, active or passive spring elements 140 and 142 may also be provided to help return the scissor mechanisms to their original configuration when the delivery of energy is stopped.

Figure 8:
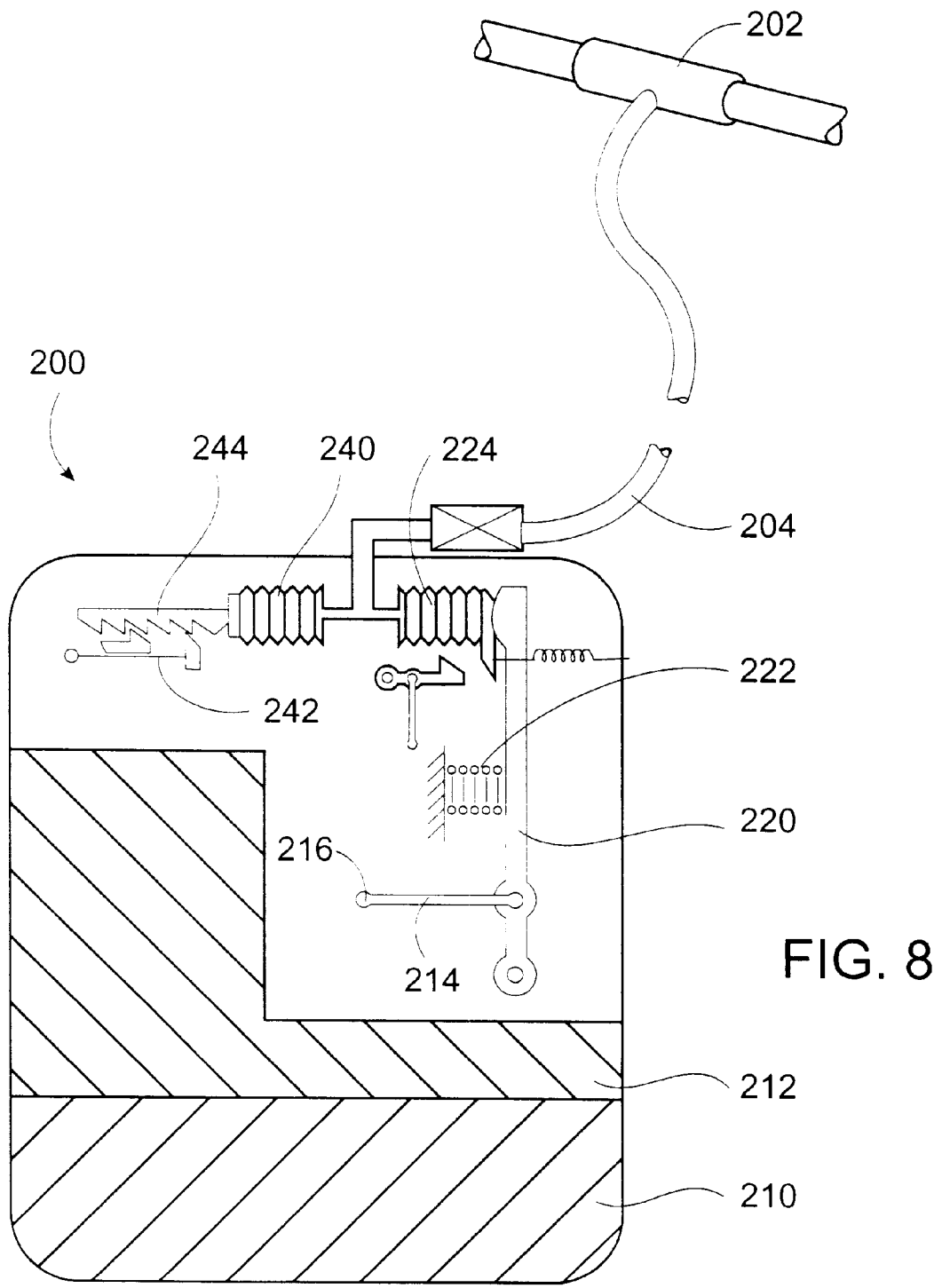
FIG. 8 illustrates a fifth embodiment of an actuator suitable for use in the system of FIG. 1.

Referring now to FIG. 8, a hydraulic control module 200 connected to an inflatable actuator 202 by a hydraulic lead 204 is illustrated. The module 200 includes a power supply 210, typically a battery, control circuitry 212, and a shape memory wire 214 for powering the system. The shape memory wire is fixed at one end 216 and attached to a lever 220 at its free end. The lever is biased by spring 222 and engages a first bellows 224 at its top end. When the control module 12 is given a signal to close, power is directed to the wire 214, causing it to shorten and deflect lever 220 toward the left, thus closing the bellows 224 to increase the pressure in cuff 202 to close the body lumen. When the power is turned off, the wire will return to its original configuration, assisted by spring 222, to open the bellows and reduce the pressure. The closing pressure can be adjusted by a second bellows 240 which can be remotely adjusted using a wire 242 and control rack 244. The bellows 240 thus increases or relieves the system pressure in order to effect the ultimate closing pressure provided by the inflatable cuff 202. The bellows 240 may be controlled through the control circuitry 212 using the remote programmer 42 (FIG. 1).

Systems of the present invention may be combined in kits 300 as illustrated in FIG. 9. The kits may comprise any one or more of the system components, including the remote switch actuator 30, programmer 42, lead 16, actuator 14, control module 12, implantation tools 306, and optionally instructions for use 302. The instructions for use may set forth any of the instructions for using and/or implanting the system in a patient. Typically, at least the implantable components will be sterilized and provided in a sterile package 304. In a first exemplary case, a kit may comprise an actuator, a control module, implantation tools 306, and a remote switch actuator, together with instructions for using the implanted system according to any of the methods described above. In a second exemplary case, the kit may comprise an actuator, a control module, a lead for connecting the actuator to the control module, and implantation tools 306, together with instructions for implanting the components according to any of the protocols described above.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An implantable system for selectively opening and closing a body lumen, said system comprising:
   a control module including a power source and a remotely operated switch which controls an output from the power source to produce a pressurized inflation medium; and
   an actuator comprising an inflation cuff connectable to receive the pressurized inflation medium from the output on the control module, wherein said cuff is mountable over an exterior of the body lumen and shifts between an open configuration where the body lumen is at least partially open and a closed configuration where the body lumen is closed in response to a change in power from the output controlled by the switch.

2. A system as in claim 1, further comprising a remote switch actuator.

3. A system as in claim 2, wherein the remote switch actuator comprises a magnet.

4. A system as in claim 1, further comprising an implantable hydraulic lead which connects the output of the control module to the actuator.

5. A system as in claim 4, wherein the lead has a connector at at least one end to permit selective connection to the control module or the actuator.

6. A system as in claim 4, wherein the lead has two connectors for selective connection to both the control module and the actuator.

7. A system as in claim 1, wherein the control module further includes a programmable component which modulates at least one variable selected from the group consisting of opening time, opening diameter, opening force, and closing force.

8. A system as in claim 7, wherein the programmable component is remotely programmable.

9. A system as in claim 8, further comprising a remote programmer which can download program information to the programmable component of the control module.

10. A system as in claim 9, wherein the remote programmer provides wireless communication between the programmer and the programmable component of the control module.

11. A system as in claim 9, wherein the control module includes a status report component and wherein the programmer can retrieve the status of operational variables from the status report component.

12. A system as in claim 11, wherein the status report component includes readings of at least one of battery life, opening time, opening diameter, opening force, and closing force.

13. An implantable system for selectively opening and closing a body lumen, said system comprising:
    a control module including a power source, a remotely operated switch which controls an output from the power source and a remotely programmable component which modulates at least one variable selected from the group consisting of opening time, opening diameter, opening force, and closing force;
    an actuator connectable to receive power from the output on the control module, wherein said actuator couples to an exterior of the body lumen and shifts between an open configuration where the body lumen is at least partially open and a closed configuration where the body lumen is closed in response to a change in power from the output controlled by the switch;
    a remote switch actuator for turning the power source on and off in the control module; and
    a remote programmer which can download program information to the remotely programmable component of the control module.

14. A system as in claim 13, wherein the remote switch actuator comprises a magnet.

15. A system as in claim 13, further comprising an implantable electrical or hydraulic lead which connects the output of the control module to the actuator.

16. A system as in claim 15, wherein the lead has a connector at at least one end to permit selective connection to the control module or the actuator.

17. A system as in claim 15, wherein the lead has two connectors for selective connection to both the control module and the actuator.

18. A system as in claim 13 wherein the control module includes a status report component and wherein the programmer can retrieve the status of operational variables from the status report component.

19. A system as in claim 18, wherein the status report component includes readings of at least one of battery life, opening time, opening diameter, opening force, and closing force.

* * * * *